United States Patent [19]

Knifton et al.

[11] 4,299,985

[45] Nov. 10, 1981

[54] SELECTIVE OXOAMINATION PROCESS

[75] Inventors: John F. Knifton; Philip H. Moss, both of Austin, Tex.

[73] Assignee: Texaco Inc., White Plains, N.Y.

[21] Appl. No.: 217,287

[22] Filed: Dec. 16, 1980

Related U.S. Application Data

[63] Continuation-in-part of Ser. No. 778,817, Mar. 17, 1977, abandoned.

[51] Int. Cl.$^3$ .................... C07C 85/08; C07C 45/50
[52] U.S. Cl. .................... 564/467; 564/473; 568/423; 568/454
[58] Field of Search ............ 564/467, 473; 568/423, 568/454

[56] References Cited

U.S. PATENT DOCUMENTS

| | | | |
|---|---|---|---|
| 3,067,255 | 12/1962 | Scholz et al. | 564/467 |
| 3,520,933 | 7/1970 | Adam et al. | 564/467 |
| 3,981,925 | 9/1976 | Schwager et al. | 568/423 |
| 4,036,883 | 7/1977 | Voges et al. | 564/480 |

FOREIGN PATENT DOCUMENTS

| | | | |
|---|---|---|---|
| 1817691 | 6/1970 | Fed. Rep. of Germany | 564/473 |
| 45-32408 | 10/1970 | Japan | 564/467 |

*Primary Examiner*—John Doll
*Attorney, Agent, or Firm*—Carl G. Ries; Robert A. Kulason; Carl G. Seutter

[57] ABSTRACT

This invention concerns the synthesis of linear alkyl primary amines from a-olefins via an oxoamination process comprising (a) hydrogen and carbon monoxide addition to olefinic substrates to obtain aldehyde-containing compounds in the presence of ligand-stabilized platinum(II) halide catalysts with Group IVB metal halide cocatalysts, and (b) reductive amination of said aldehydic intermediates in the presence of oxide-supported, nickel catalysts.

8 Claims, No Drawings

SELECTIVE OXOAMINATION PROCESS

This application is a continuation in part application of our copending application Ser. No. 778,817, filed Mar. 17, 1977, now abandoned.

SUMMARY OF INVENTION

This invention concerns a process for the oxoamination of alpha ($\alpha$) olefins to linear alkyl primary amines without the need for isolating the intermediate linear alkyl aldehydes.

More particularly, this invention relates to the catalytic oxoamination of $\alpha$-olefins to linear alkyl primary amines using first, a ligand stabilized platinum(II) halide-Group IVB metal halide for the catalytic addition of hydrogen and carbon monoxide to said olefinic substrates to obtain linear alkyl aldehydes as intermediates, then reductively aminating said alkyl aldehydes to the desired linear alkyl amines through the addition of hydrogen and ammonia in the presence of oxide-supported nickel catalysts.

BACKGROUND OF THE INVENTION

Large quantities of linear alkyl primary amines are presently produced commercially from the natural fatty acids in coconut oil, palm oil, tallow, etc. The market for these amines exceeds 100 MM lbs/yr, with applications in the rubber and detergent industries and as chemical intermediates. This invention concerns the synthesis of linear alkyl primary amines from a petrochemical source, viz, $\alpha$-olefins, via an oxoamination process. Said process comprises (a) hydroformylation of linear alkyl $\alpha$-olefin substrates to the corresponding straight-chain aldehydes containing one more carbon atom (Eq. 1) and (b) amination of said linear aldehyde to the corresponding desired linear alkyl primary amine (Eq. 2).

$$RCH=CH_2 + CO + H_2 \rightarrow RCH_2-CH_2-CHO \quad (1)$$

$$RCH_2-CH_2-CHO + NH_3 + H_2 \rightarrow RCH_2-CH_2-CH_2-NH_2 + H_2O \quad (2)$$

After an extensive research program the applicants have developed a class of ligand-stabilized platinum(II)-Group IVB metal halide catalysts for step 1 which as the advantages of:

(1) High selectivity to the linear aldehyde in step 1 with little branched aldehyde contaminant (2) Ease of separation of the intermediate aldehydes from the platinum catalyst, particularly in the case of dispersions of the ligand-stabilized platinum(II) halide catalyst in quarternary ammonium salts of trichlorostannate(II), without the need to destroy, or precipitate, the catalyst as in analogous, cobalt 'Oxo' technology.

(3) Furthermore, said dispersions of ligand-stabilized platinum(II) halide catalysts in quaternary ammonium salts of trichlorostannate(II) remain active after linear aldehyde recovery and may be recycled with fresh $\alpha$-olefin charge, thereby achieving additional linear aldehyde syntheses.

The class of oxide-supported nickel-containing catalysts developed by the applicants for step 2, the reductive amination of the linear aldehyde intermediates to linear alkyl primary amines, also have the intrinsic advantages of:

(1) Exhibiting high selectivity to said linear alkyl primary amine with little formation of branched alkyl or secondary amine formation. and (2) Good specific activity, which allows the reductive amination reaction to be carried out rapidly under moderate conditions of temperature and pressure.

PRIOR ART

It is known in the art how to prepare aldehydes from olefinic substrates such as ethylene, propylene or 1-butene using carbon monoxide and hydrogen at elevated temperatures and pressures. Normally these processes are catalytic and are conducted in the presence of homogeneous or heterogeneous catalysts (see equations shown above). Similarly, it is known how to reduce the aldehyde intermediates to the corresponding amines using a great variety of catalysts, supported (heterogeneous) and non-supported (homogeneous). A typical sampling of the processes used to form the aldehydes from olefins (hydroformylation) include U.S. Pat. Nos. 3,981,925, 3,657,368 and U.K. Pat. No. 1,138,601. The second stage of the overall process, that is the reduction of aldehydes to amine products, is broadly set forth in the literature and specific patents will not be set forth.

However, the selective reduction of aldehyde intermediates, such as have been produced by the first catalytic transformation, without the need for isolating the aldehyde, is believed to be novel in the art particularly when using these oxide-supported, nickel-containing catalysts.

In view of this unusual combination of advantages, the inventive process represents an improvement in substance in view of the art.

In the broadest contemplated practice of this invention, substantial quantities of linear alkyl primary amines are produced by the oxoamination of alpha olefin substrates containing 2 to 30 carbon atoms by the step of:

(a) forming a hydroformylation reaction mixture of olefin substrate, carbon monoxide, hydrogen and from about 0.001 to 0.1 moles of a three-component, ligand-stabilized, platinum(II) halide catalyst per mole of olefin substrate, said catalysts being selected from the group consisting of:

$PtCl_2[P(C_6H_5)_3]_2 + SnCl_2$
$PtCl_2[P(p-CH_3.C_6H_4)_3]_2 + SnCl_2$
$PtCl_2[P(n-C_4H_9)_3]_2 + SnCl_2$
$PtCl_2[P(C_6H_5)_3]_2 + SnCl_4$
$PtCl_2[P(C_6H_5)_3]_2 + GeCl_2$
$PtCl_2[P(CH_3)_2C_6H_5]_2 + SnCl_2$
$PtCl_2[Ph_2AsCH_2CH_2AsPh_2] + SnCl_2$
$PtCl_2]P(OC_6H_5)_3]_2 + SnCl_2$
$PtCl_2[As(C_6H_5)_3]_2 + SnCl_2$
$PtCl_2[S(C_6H_5)_2]_2 + SnCl_2$
$PtBr_2[P(C_6H_5)_3]_2 + SnBr_2$
$PtCl_2[Ph_2PCH_2CH_2PPh_2] + SnCl_2$
$PtCl_2[Sb(C_6H_5)_3]_2 + SnCl_2$
$PtCl_2(o\text{-Phenanthroline}) + SnCl_2$
$PtCl_2[P(C_6H_5)_2 + [Cl_3Sn][N(C_2H_5)_4]$
$PtCl_2[P(C_6H_5)_3]_2 + [Cl_3Sn][P(C_6H_5)_3CH_2Cl]$
$PtCl_2[P(C_6H_5)_3]_2 + [Cl_3Sn][N(n-C_4H_9)_4]$
$PtCl_2[P(C_6H_5)_3]_2 + [Cl_3Sn][As(C_6H_5)_4]$
$PtCl_2[P(C_6H_5)_3]_2 + [Cl_3Sn][N(C_7H_{15})_4]$
$PtCl_2[P(C_6H_5)_3]_2 + [Cl_3Ge][N(C_2H_5)_4]$
$PtCl_2[P(p-CH_3.C_6H_4)_3]_2 + [Cl_3Sn][N(C_2H_5)_4]$
$PtCl_2[P(n-C_4H_9)_3]_2 + [Cl_3Sn][N(C_2H_5)_4]$ the carbon monoxide and hydrogen being present in quantities sufficient to satisfy the stoichiometry of the hydroformylation reaction, (b) pressurizing the hydroformylation reaction mixture between about 100 psig to about 3000 psig and heating the pressurized reaction mixture at about 25° C. to about 125° C. until a major amount of linear alkyl aldehyde products and a minor amount of non-linear alkyl aldehyde products are formed, and (c) contacting said linear alkyl aldehyde products with at least sufficient hydrogen and ammonia to satisfy the stoichiometry of reducing the linear alkyl aldehyde to linear alkyl primary amine product, pressurizing between about 100 psig to about 3000 psig and heating said linear alkyl aldehyde from about 25° to about 200° C., in the presence of oxide supported nickel catalyst containing from 5% to about 75 weight % nickel until a substantial amount of linear alkyl primary amine product is formed, and (d) isolating the linear alkyl primary amine product contained therein.

A. PROCESS SEQUENCE AND VARIATIONS

In general, the components of the hydroformylation reaction mixture, including optional inert solvent, olefin and platinum catalyst may be added in any sequence as long as good agitation is employed to provide a good dispersion or a homogeneous reaction mixture. For example, the following represent some variations insofar as the addition of catalyst components, inert solvents and olefin addition that may be made without departing from the inventive process. These modifications include:

(1) The catalyst may be preformed and added preformed to the reaction solvent prior to the addition of the olefin and other inert solvent components.

(2) Preferably, to minimize stability problems with the catalyst, the catalyst is best formed in situ usually by mixing the deoxygenated inert solvent and neat olefin, followed by the addition of the excess metal halide of Group IVB, and finally by the addition of the ligand stabilized platinum(II) complex to form the reaction mixture.

(3) After using either variation 1 or 2, the deoxygenated catalyst containing reaction mixture is pressurized with CO and hydrogen and heated until the aldehyde product is formed.

(4) An especially preferred modification, which minimizes both the induction period and the isomerization of the olefin, is the following: the catalyst is formed in a deoxygenated solvent; the catalyst solution is pressurized with carbon monoxide and hydrogen and heated to the desired reaction temperature; olefin is then added neat or dissolved in a suitable solvent. The reaction mixture is agitated under CO and $H_2$ at the desired reaction temperature until the aldehyde product is formed.

(5) A second preferred modification, is the use of dispersions of said ligand-stabilized platinum(II) halide complexes in low-melting quaternary alkyl salts of trichlorostannate(II) or trichlorogermanate(II) as catalysts for the conversion of alpha-olefins to the corresponding linear alkyl aldehyde.

B. LIGAND-STABILIZED PLATINUM HYDROFORMYLATION CATALYSTS

Some ligand-stabilized, platinum(II) halide, Group IVB metal halide complexes are known in the literature and methods for their preparation have been described*. One convenient mode of preparation in situ is to mix a solution of platinum(II) halide complex such as $PtCl_2[(C_6H_5)_3]_2$, with a large molar excess of Group IVB metal halide, preferentially $SnCl_2$.

*For example: R. D. Cramer et al, J. A. Chem. Soc., 85, 1691 (1963).

The three component ligand-stabilized platinum(II) catalyst composition of this invention consists essentially of:

1. platinum(II) halides
2. Group VB, VIB, or VIIB donor ligands, and
3. Group IVB metal halides 1. The platinum(II) halide components employed in the catalyst composition are preferably the dichloride or the dibromide, in that order. These dihalides, in order to be effective for the selective and preferential hydroformylation process, must include at least one Group VB, VIB or VIIB donor ligand and Group IVB metal halides, described more fully below:

2. Each Group VB donor ligand contains one or more phosphorus antimony or arsenic atoms, preferably in the trivalent state, bonded to one or more hydrocarbyl radicals, said radicals being selected from the group consisting of aryl, alkyl, and substituted aryl radicals containing less than 20 carbon atoms. Illustrative examples of suitable Group VB donor ligands are $P(C_6H_5)(CH_3)_2$, $P(C_6H_5)_3$, $As(C_6H_5)_3$, $P(n-C_4H_9)_3$, $P(OC_6H_5)_3$, $P(P-CH_3.C_6H_4)_3$ and $(C_6H_5)_2PCH_2CH_2P(C_6H_3)_2$.

3. Group IVB metal halides which can be utilized with the first two components [platinum(II) halides and Group VB, VIB or VIIB donor ligands] include tin(II) chloride, tin(II) bromide, tin(II) iodide, tin(IV) chloride, and germanium(II) chloride.

Illustrative of suitable ligand-stabilized platinum(II) halide-Group IVB metal halide selective hydroformylation catalysts are:

$PtCl_2[As(C_6H_5)_3]_2$—$SnCl_2$,
$PtCl_2[P(C_6H_5)_3]_2$—$SnCl_2$,
$PtCl_2[P(C_2H_5)_2(C_6H_4)]$—$SnCl_2$,
$PtCl_2[As(n-C_4H_9)_3]_2$—$SnCl_2$,
$PtCl_2[PCl(C_6H_5)_2]_2$—$SnCl_2$,
$PtCl_2[(C_6H_5)_2P(CH_2)_2P(C_6H_5)_2]$—$SnCl_2$,
$PtCl_2[(C_6H_5)_2AsCH_2CH_2As(C_6H_5)_2]$—$SnCl_2$,
$PtCl_2[P(n-C_4H_9)_3]_2$—$SnCl_2$,
$PtCl_2[P(CH_3)_2C_6H_5]_2$—$SnCl_2$,
$PtCl_2[P(p-CH_3OC_6H_4)_3]_2$—$SnCl_2$,
$PtCl_2[P(OC_6H_5)_3]_2$—$SnCl_2$,
$PtCl_2[P(p-CH_3.C_6H_4)_3]_2$—$SnCl_2$,
$PtCl_2[S(C_6H_5)_2]_2$—$SnCl_2$
$PtCl_2[Sb(C_6H_5)_3]_2$—$SnCl_2$
$PtCl_2$(o-phenanthroline)—$SnCl_2$
$K_2PtCl_4$—$SnCl_2$ as well as the corresponding tin(II) bromide, tin(II) iodide, tin(IV) chloride, and germanium(II) halide complexes. Tables I to IV show evidence of the suitability of the above class of ligand-stabilized platinum(II)-Group IV metal halides complexes as selective and preferentially hydroformylation catalysts.

A preferred class of suitable hydroformylation catalysts consists of dispersions of certain ligand-stabilized platinum(II) halide in quaternary ammonium, phosphonium, and/or arsonium salts of trichlorostannate(II) or trichlorogermanate(II). Illustrative examples of such platinum catalyst compositions which have been found active for the selective hydroformylation of linear α-olefins to linear aldehydic products include:

$[(C_2H_5)_4N][SnCl_3]$—$PtCl_2[P(C_6H_5)_3]_2$
$[(n-C_4H_9)_4N][SnCl_3]$—$PtCl_2[P(C_6H_5)_3]_2$

[(C$_6$H$_5$)$_4$As][SnCl$_3$]—PtCl$_2$[P(C$_6$H$_5$)$_3$]$_2$
[(C$_7$H$_{15}$)$_4$N][SnCl$_3$]—PtCl$_2$[P(C$_6$H$_5$)$_3$]$_2$
[(C$_2$H$_5$)$_4$N][GeCl$_3$]—PtCl$_2$[P(C$_6$H$_5$)$_3$]$_2$
[(C$_2$H$_5$)$_4$N][SnCl$_3$]—PtCl$_2$[P(p—CH$_3$.C$_6$H$_4$)$_3$]$_2$
[(C$_2$H$_5$)$_4$N][SnCl$_3$]—PtCl$_2$[P(n-C$_4$H$_9$)$_3$]$_2$
[(C$_2$H$_5$)$_4$N][SnCl$_3$—PtCl$_2$(CH$_3$)$_2$C$_6$H$_5$]$_2$

Preferably said quaternary salts should be low-melting quaternary alkyl salts of trichlorostannate(II).

C. RATIO OF TIN(II) HALIDE TO LIGAND-STABILIZED PLATINUM(II) COMPLEX

While the molar ratio of tin(II) chloride to the ligand-stabilized platinum(II) halide complex is not critical, the experimental work performed indicates that at least 1 mole of tin(II) chloride for each mole of ligand-stabilized platinum(II) chloride complex is required for reproducibility and good selectivity. Preferably a ratio of from about 2 to 8 moles of tin(II) chloride for each mole of ligand-stabilized platinum(II) complex has been established to give the optimum amount of linear paraffinic aldehyde at greatly increased rates of hydroformylation. This preferred ratio is based upon the hydroformylation of 1-heptene.

D. OXIDE-SUPPORTED, NICKEL-CONTAINING AMINATION CATALYSTS

The oxide-supported, nickel-containing amination catalysts of this invention are obtained by the coprecipitation of various nickel salts, as their carbonates or bicarbonates, in the presence of other metal salts selected from Groups IB, II, IIIB, VIA, VIIA and VII of the Periodic Table*. Preparation of said catalysts is effected by the addition of aqueous solutions of sodium carbonate, sodium bicarbonate and/or the carbonates of ammonia, to solutions of soluble nickel salts also containing the soluble salts of metals selected from Groups IB, II, IIIB, VIA, VIIA and VIII. The precipitated, carbonate-containing, material is isolated by filtration, washed, dried and calcined. The nickel content of said precipitated carbonate may vary from 5% up to about 75% by weight and said precipitated catalyst may also contain varying quantities of one or more oxides of magnesium, calcium, strontium, barium, zinc, aluminum, chromium, manganese, copper, cobalt, tungsten and iron.

*See: F. Cotton and G. Wilkinson, "Advanced Inorganic Chemistry," Interscience, 1962.

Preferred catalyst compositions consist of oxide-supported nickel catalysts containing from 5 to 7% by weight of nickel, and also containing varying quantities of two or more oxides of magnesium, barium, aluminum and chromium. Examples 42 to 51 provide exemplification of this preferred class of catalyst for effecting the reductive amination of typical linear alkyl aldehyde substantially to the desired linear alkyl primary amines.

E. REACTION TEMPERATURES

The temperature ranges which can be employed for the hydroformylation and reductive amination steps are variables which are dependent upon experimental factors including the olefin employed, the total pressure, the mole ratio of hydrogen and carbon monoxide used, the concentrations of reactants and catalyst, and particularly the choice of platinum and nickel catalysts. Starting with a typical linear α-olefin of 2 to 30 carbon atoms and PtCl$_2$[P(C$_6$H$_5$)$_3$]$_2$-SnCl$_2$ as a representative hydroformylation catalyst, an operable temperature range for the first, hydroformylation, step is from about 25° to 125° C. at superatmospheric pressures of greater than 100 psig. Likewise, the operable temperature range for the reductive amination is from about 25° to 200° C.

F. REACTION PRESSURES

The pressure range which can be employed for the hydroformylation step is a variable which is also dependent on the factors mentioned above. Using PtCl$_2$[P(C$_6$H$_5$)$_3$]$_2$—SnCl$_2$ as a representative catalyst, and 1-heptene as the linear alpha olefin component, an operable pressure range is from 100 to 3000 psig, with a mole ratio of H$_2$:CO being 1:1, when a temperature range of from about 25° to 125° C. is employed.

Likewise the total pressure of hydrogen plus ammonia applied during the reductive amination step may range from 100 to 3000 psig, or greater, using the oxide-supported nickel-containing catalysts of this invention.

G. INERT SOLVENTS

Both the hydroformylation and reductive amination steps may be run conveniently in the presence of an inert diluent. For the hydroformylation step experimental data indicate the preferred solvents are polar ketones such as acetone, methyl ethyl ketone, diethyl ketone, methyl propyl ketone, methyl isobutyl ketone, and acetophenone. However, other solvents inert to hydroformylation can be used. These include aromatics such as benzene, toluene, xylenes and the like. Generally the reaction is run in the presence of sufficient inert solvent to disperse the components of the reaction mixture; excess inert solvent does not appear to be harmful.

The preferred class of solvents for the reductive amination step are alkanols, including methanol, ethanol, isopropanol and tert. butanol.

H. REACTION TIMES REQUIRED

As previously indicated in the analogous discussion above, experimental variables are important in arriving at reaction times. Generally, substantial conversions (about 80 to 95%) of the alpha-olefin to the linear paraffinic aldehydes can almost always be accomplished within 20 hours, with 4 to 6 hours representing the more usual reaction time interval.

Likewise the reaction times for the reductive amination step may exceed 20 hours, with 4 to 6 hours again representing the more usual reaction time interval.

I. RATIO OF PLATINUM CATALYSTS TO OLEFIN SUBSTRATE

Experimental work indicates that an initial molar ratio of up to about 500 to 1000 moles of alpha-olefin per mole of platinum metal catalyst may be employed in the first, hydroformylation, step. This minimal ratio of about 0.001 moles of catalyst per mole of total olefin is herein referred to as a "catalytic ratio" or "catalytic amount." Much lower ratios (i.e. 25 moles of olefin substrate per mole of platinum catalyst complex) are not harmful but are economically unattractive. For this reason the favored mole ratio range is from 100 to 500 moles of total olefin per mole of platinum catalyst complex.

J. OLEFINS AS SUBSTRATES

Olefins ranging in carbon content from 2 up to 30 carbon atoms can be employed as substrates for the oxoamination reactions. Illustrative of suitable terminal (alpha) olefin substrates include 1-propene, 1-butene, 1-pentene, 1-hexene, 1-heptene, 1-octene, 1-nonene, 1-decene, 1-undecene, 1-dodecene, 1-tetradecene as well as their higher homologues such as 1-heptadecene, 1-octadecene, 1-eicosene, 1-tricosene, 1-pentacosene. Illustrative branched chain α-olefin substrates include isobutylene, 2-methyl-1-pentene and 3-methyl-1-pentene. Illustrative internal and cyclic olefins include 2- butene, 2-pentene, 2-heptene, and cyclohexene, etc. These olefin substrates may be utilized in conjunction with one or more inert background solvents such as those mentioned above. The olefins can be in the form of single, discrete compounds or in the form of mixtures of olefins with or without large quantities of saturated hydrocarbon. In the latter case these comprise mixtures of from 2 to 30 carbon atoms. Table VI shows data for the hydroformylation of various olefins.

K. RATIO OF HYDROGEN TO CARBON MONOXIDE

The $H_2/CO$ ratio exmployed during the hydroformylation step may vary over the range from 30/1 to 1/30 when suitable temperatures and total pressures are employed. A preferred narrower range is from 2/1 to ½ of hydrogen to carbon monoxide.

L. IDENTIFICATION PROCEDURES are by one or more of the following analytical procedures—gas chromatography (gc), infrared, elemental analysis and nuclear magnetic resonance. Unless otherwise specified all percentages are by mole rather than weight or volume, and all temperatures are in centigrade rather than fahrenheit.

M. CONVERSION as defined herein represents the extent of conversion of the reacting olefin to other products. Conversion is expressed as a percentile and is calculated by dividing the amount of olefin or intermediate aldehyde consumed during the hydroformylation or reductive amination steps, respectively, by the amount originally charged, and multiplying the quotient by 100.

N. YIELD as defined herein, represents the efficiency in catalyzing the desired hydroformylation or reductive amination reaction relative to other undesired reactions. In this instance linear alkyl primary amine formation is the desired conversion. Yield is expressed as a percentile, and is calculated by determining the amount of linear alkyl primary amine or linear aldehydic intermediate formed, divided by the amount of aldehyde or olefin charged and multiplying the quotient obtained by 100.

O. SELECTIVITY as defined herein is the efficiency in catalyzing a desired hydroformylation or reductive amination reaction relative to other undesired reactions. When α-olefins are to be hydroformylated, hydroformulation to the linear paraffinic aldehyde is the desired coversion. Selectivity is expressed as a percentile, and is calculated by determining the amount of linear aldehyde product formed, divided by the total amount of aldehyde products formed and multiplying the quotient obtained by 100.

Having described the inventive process in general terms, the following examples are submitted to supply specific and illustrative embodiments.

EXAMPLE 1

Hydroformylation of 1-Heptene Catalyzed by Bis(Triphenylphosphine)Platinum(II) Chloride—Stannous Chloride Catalyst Complex To a 350 ml glass liner of a rocking autoclave is added 58 ml of methyl isobutyl ketone and 7.9 ml (0.058 mole) of 1-heptene. The solution is deoxygenated with nitrogen and 0.325 g ($1.45 \times 10^{-3}$ mole) of $SnCl_2.2H_2O$ is added to the mixture and stirred 2-3 minutes until dissolved. Then $PtCl_2(PPH_3)_2$, 0.229 g ($2.9 \times 10^{-4}$ mole), is added, and the mixture stirred for a further 2-3 minutes under a nitrogen purge. The catalyst solution turns to a light yellow-greenish color, and although some of the $PtCl_2(PPh_3)_2$ initially remains undissolved, the mixture becomes completely homogeneous after a short period of warming and stirring under carbon monoxide and hydrogen. The loaded liner is then added to the autoclave and the apparatus is deoxygenated with nitrogen. Carbon monoxide, 750 psig, and hydrogen, 750 psig, are then charged to the reactor and the reactor is heated to 66° C. with rocking for 3 hours, and the heat turned off.

After the apparatus is cooled and vented, 62 ml of a greenish-red solution containing a small amount of dark solids is recovered. Gas chromatographic analysis reveals the following results:

| | |
|---|---|
| Conversion (mole %) | 100 |
| Yield $C_6$ aldehydes (mole %) | 85 |
| Mole ratio 1-octylaldehyde/2-methyl heptaldehyde | 9/1 |
| Isomerization of 2- and 3-heptane (mole %) | 2.7 |

The missing 8.7 mole percent of 1-heptene is assumed to have formed high boiling products which do not come off the gas chromatograph under the conditions at which it was operated.

EXAMPLE 1A

Oxoamination of 1-Heptene to n-Octylamine Catalyzed by a Platinum(II)-Stannous Chloride Catalyst Plus an Oxide-Supported Nickel Catalyst To a 350 ml glass liner of a rocking autoclave is added 58 ml of toluene and 7.9 ml (0.058 mole) of 1-heptene. The solution is deoxygenated with nitrogen and 0.325 g ($1.45 \times 10^{-3}$ mole) of $SnCl_2.2H_2O$ is added to the mixture and stirred 2-3 minutes until dissolved. Then $PtCl_2(PPh_3)_2$, 0.229 g ($2.9 \times 10^{-4}$ mole), is added, and the mixture stirred for a further 2-3 minutes under a nitrogen purge. The catalyst solution turns to a light yellow-greenish color, and although some of the $PtCl_2(PPh_3)_2$ initially remains undissolved, the mixture becomes completely homogeneous after a short period of warming and stirring under carbon monoxide and hydrogen. The loaded liner is then added to the autoclave and the apparatus is deoxygenated with nitrogen. Carbon monoxide, 750 psig, and hydrogen, 750 psig, are then charged to the reactor and the reactor is heated to 66° C. with rocking for 3 hours, and the heat turned off. G.C. confirms $C_8$ aldehyde yield of about 0.049 mole.

To the above glass liner containing 0.049 mole octylaldehyde are added ten g of the oxide-supported nickel catalyst prepared according to the procedure of example 42 and 30 ml of methanol. The reaction vessel is deoxygenated, 10 g of ammonia injected in from the side ampoule, and the whole pressured to 1200 psig with hydrogen. The reaction mixture is then heated to 100° C. with agitation, and held at temperature for four hours.

After cooling and venting, the liquid product is separated from the solid catalyst by filtration and subjected to analysis by G.C. A four g yield of octylamines is isolated by fractional distillation giving a selectivity of 88 mole % to n-octylamine and a yield of 0.031 mole of octylamines.

EXAMPLES 2-5

Hydroformylation of 1-Heptene Catalyzed by Platinum Bimetallic Complexes—Effect of Group IBV Metal Halide Composition Table I which follows, shows the data obtained when the designated catalysts are employed in the hydroformylation of 1-heptene using the procedure of Example 1. All the examples shown in Table I were carried out under the following conditions:

Solvent—methyl isobutyl ketone
1-Heptene, 0.88 mole per liter
1-Heptene/$PtCl_2(PPh_3)_2$ molar ratio, 200/1
$MCl_n$/$PtCl_2(PPh_3)_2$ molar ratio, 5/1
$H_2$/CO=1/1, 1500 psig
Reaction temperature, 66° C.

As the data of Table I indicate, meaningful hydroformylation of 1-heptene to octyl aldehyde is obtained under our preferred mild reaction conditions when a ligandstabilized platinum halide complex and the Group IVB metal halide exemplified by stannous chloride, stannic chloride, and germanium(II) chloride, are used together to form a catalyst. In the absence of these Group IVB metal halides such ligand-stabilized platinum halide complexes are not effective hydroformylation catalysts under our preferred mild reaction conditions.

EXAMPLES 6-11

Hydroformylation of 1-Heptene Catalyzed by Platinum Bimetallic Complexes-Effect of Halogen, Pseudo-Halogen and Stannous Halide Composition Table II which follows, shows the data obtained when the designated catalysts are employed in the hydroformylation of 1-heptene using the procedure of Example 1. All the examples shown in Table II were carried out under the conditions described in Example 1 and Table I.

As the data of Table II indicate, meaningful hydroformylation of 1-heptene to octyl aldehyde is obtained under our preferred mild reaction conditions when ligand stabilized platinum halide complexes and stannous halide metal salts are used together to form a catalyst. The effectiveness of the halides is in the direction Cl>Br>I. The pseudo-halide cyanide ligand was not effective in promoting hydroformylation by the catalyst $Pt(CN)_2(PPh_3)_2$ under our preferred mild reaction conditions.

EXAMPLES 12-18

Hydroformylation of 1-Heptene Catalyzed by Platinum Bimetallic Complexes—Effect of Ligands with Groups VB, VIB, VIIB Donor Atoms Table III which follows, shows the data obtained when the designated catalysts are employed in the hydroformylation of 1-heptene using the procedure of Example 1.

TABLE I

| | | Mole % | | | | | |
|---|---|---|---|---|---|---|---|
| Example | Group IVB metal halide | 1-Heptene conversion | Total yield aldehydes | Selectivity 1-aldehyde | Isomerization to 2,3-heptenes | Reduction to n-heptane | Missing product |
| 2 | None | 0 | — | — | — | — | — |
| 3 | $SnCl_2$ | 100 | 85 | 90 | 3.6 | 2.7 | 9 |
| 4 | $GeCl_2$[a] | 14 | 14 | 98 | — | — | — |
| 5 | $SnCl_4$ | 100 | 50 | 84 | 6.5 | 8.5 | 35 |

[a]$GeCl_2$ complex not completely solubilized

TABLE II

| | | Mole % | | | | | |
|---|---|---|---|---|---|---|---|
| Example | $PtX_2(PPh_3)_2$ + $SnX_2$ | 1-Heptene conversion | Total yield aldehydes | Selectivity 1-aldehyde | Isomerization to 2,3-heptenes | Reduction to n-heptane | Missing product |
| 6 | $PtCl_2(PPh_3)_2$ + $SnX_2$ | 100 | 85 | 90 | 3.6 | 2.7 | 9 |
| 7 | $PtBr_2(PPh_3)_2$ + $SnBr_2$ | 100 | 64 | 85 | 6.2 | 2.6 | 28 |
| 8 | $PtI_2(PPh_3)_2$ + $SnI_2$[a] | <2 | 0.6 | — | — | — | — |
| 9 | $Pt(CN)_2(PPh_3)_2$ | 0 | — | — | — | — | — |
| 10 | $PtCl_2(AsPh_3)_2$ + $SnCl_2$ | 100 | 46 | 75 | 10 | 9 | 35 |
| 11 | $PtI_2(AsPh_3)_2$ + $SnI_2$[a] | 6.5 | 1.6 | 88 | — | — | 4.9 |

[a]Catalyst not completely solubilized

TABLE III

| | | Mole % | | | | | |
|---|---|---|---|---|---|---|---|
| Example | Platinum complex | 1-Heptene conversion | Total yield aldehydes | Selectivity 1-aldehyde | Isomerization to 2,3-heptenes | Reduction to n-heptane | Missing product |
| 12 | $PtCl_2(PPh_3)_2$ + $SnCl_2$ | 100 | 85 | 90 | 3.6 | 2.7 | 9 |
| 13 | $PtCl_2(AsPh_3)_2$ + $SnCl_2$ | 100 | 46 | 75 | 10 | 9 | 35 |
| 14 | $PtCl_2(Ph_2AsCH_2CH_2AsPh_2)$ + $SnCl_2$[a] | 100 | 60 | 81 | 7 | 27 | 10 |
| 15 | $PtCl_2(SbPh_3)_2$ + $SnCl_2$ | 94 | 61 | 75 | 12 | 8 | 13 |
| 16 | $PtCl_2$(o-Phenanthroline) + $SnCl_2$[a] | 96 | 56 | 71 | 15 | 8 | 17 |
| 17 | $PtCl_2(SPh_2)_2$ + $SnCl_2$ | 91 | 52 | 72 | 9 | 8.0 | 22 |
| 18 | $PtCl_4K_2$ + $SnCl_2$ | 99 | 60 | 73 | 13 | 10 | 16 |

[a]Catalyst not completely solubilized

As the data of Table II indicate, meaningful hydroformylation of 1-heptene to octyl aldehyde is obtained under our preferred mild reaction conditions when a variety of ligands containing Group VB, VIB and VIIB donor atoms are used to stabilize the platinum halide complexes together with the stannous halide metal salts to form a catalyst. The preferred ligands appear to be those containing a trivalent phosphorus donor atom.

EXAMPLES 19-25

Hydroformylation of 1-Heptene Catalyzed Platinum Bimetallic Complexes—Effect of Trivalent Phosphorous Ligands Table IV which follows shows the data obtained when the designated catalysts are employed in the hydroformylation of 1-heptene using the procedure of Example 1. All the examples shown in Table IV were carried out under the conditions described in Example 1 and Table I.

As the data of Table IV indicate, meaningful hydroformylation of 1-heptene to octyl aldehyde is obtained under our preferred mild reaction conditions when a variety of trivalent organo-phosphorous ligands are used to modify Pt(II) chloride—stannous chloride catalysts. These include triaryl, trialkyl, substituted triaryl and mixed alkyl, aryl phosphines. Triaryl phosphites, such as triphenyl phosphite, are also suitable. Complexes with mixed substituted phosphines, such as $PCl(Ph)_2$, are active, as are complexes with bidentate phosphines such as $Ph_2PCH_2CH_2PPh_2$.

column of 20% OS-124 on chromasorb "G" heated to 120° C. with 100 cc/min. He flow.

| | |
|---|---|
| Yield of isolated butyraldehydes | 34.5 grams |
| Yield of isolated butyraldehydes (basis propylene charged) | 48 mole % |
| Purity of isolated butyraldehydes | 99% |
| Selectivity to n-butyraldehyde | 82% |

The recovered crystalline melt catalyst remains an active hydroformylation catalyst after butyraldehyde recovery by decantation. Additional n-butyraldehyde may be prepared simply by recycling the used dispersion of platinum catalyst in quaternary alkyl trichlorostannate(II) salt with fresh propylene under the hydroformylation conditions describer supra. Yield data for the isolated butyraldehydes prepared over a three cycle experiment using the same sample of bis(triphenylphosphine)platinum(II) chloride dispersed in tetraethylammonium trichlorostannate(II) are summarized in Table V.

EXAMPLES 27-34

Hydroformylation of Propylene Catalyzed by Ligand-Stabilized Platinum(II) Complexes Dispersed in Various Quaternary Salts of Trichlorostannate(II) and Trichlorogermanate(II)

In these examples the hydroformylation of propylene to n-butyraldehyde is carried out in accordance with the procedure of Example 26, but in the presence of various ligand-stabilized platinum(II) complexes dis-

TABLE IV

| | | Mole % | | | | | |
|---|---|---|---|---|---|---|---|
| Run | Platinum complex | 1-Heptene conversion | Total yield aldehydes | Selectivity 1-aldehyde | Isomerization to 2,3-heptenes | Reduction to n-heptane | Missing product |
| 19 | $PtCl_2[PPh_3]_2$ + $SnCl_2$ | 100 | 85 | 90 | 3.6 | 2.7 | 9 |
| 20 | $PtCl_2[Ph_2PCH_2CH_2PPh_2]$ + $SnCl_2$<sup>a</sup> | 42 | 31 | 78 | 5.8 | 4.1 | 1 |
| 21 | $PtCl_2[P(n-Bu)_3]_2$ + $SnCl_2$ | 100 | 83 | 89 | 7.9 | 2.5 | 6 |
| 22 | $PtCl_2[PPh(CH_3)_2]_2$ + $SnCl_2$ | 78 | 59 | 87 | 9.7 | 6.3 | 3 |
| 23 | $PtCl_2[P(p-CH_3 . C_6H_4)_3]_2$ + $SnCl_2$ | 90 | 78 | 93 | 8.9 | 1.9 | — |
| 24 | $PtCl_2[P(OPh)_3]_2$ + $SnCl_2$ | 100 | 45 | 73 | 19 | 16 | 20 |
| 25 | $PtCl_2[PCl(Ph)_2]_2$ + $SnCl_2$ | 100 | 72 | 89 | 13.6 | 5.4 | 9 |

<sup>a</sup>Catalyst not completely solubilized

EXAMPLE 26

Hydroformylation of Propylene Catalyzed by Bis(Triphenylphosphine) Platinum(II) Chloride Dispersed in Tetraethylammonium Trichlorostannate(II)

An appropriately sized reaction vessel, such as an autoclave, equipped with heating, cooling, agitating, pressurizing means, and a side ampoule system for introducing charges under operating conditions, is charged with a sample of tetraethylammonium trichlorostannate(II) (14.2 g 40 mmole) and bis(triphenylphosphine)platinum(II) chloride (3.16 g 4.0 mmole). The reactor sealed, purged with CO, and pressured to 1260 psig with 42 g of propylene (1 mole) plus a 1:1 (V/V) gas mixture of $CO/H_2$. The mixture is heated to 80° C., stirred for 5 hours at temperature, and allowed to cool. Forty grams of yellow liquid product are recovered by decantation from the yellow crystalline melt, and fractionally distilled. Butyraldehydes (34.5 g 0.48 mole) are recovered from a fraction boiling 72°–75° C. (1 atm), and analyzed by gas chromatography using a 10 ft × ¼"

persed in a number of quaternary ammonium, phosphonium and arsonium salts of trihalostannate(II) and trihalogermanate(II). Under otherwise constant conditions of temperature, pressure and propylene-to-Pt ratios, n-butyraldehyde was the major hydroformylation product with each of the following catalyst dispersions.

| Example | Catalyst composition |
|---|---|
| 27 | $[ClCH_2(C_6H_5)_3P][SnCl_3]=PtCl_2[P(C_6H_5)_3]_2$ |
| 28 | $[(n-C_4H_9)_4N][SnCl_3]=PtCl_2[P(C_6H_5)_3]_2$ |
| 29 | $[(C_6H_5)_4As][SnCl_3]=PtCl_2[P(C_6H_5)_3]_2$ |
| 30 | $[(C_7H_{15})_4N][SnCl_3]=PtCl_2[P(C_6H_5)_3]_2$ |
| 31 | $[(C_2H_5)_4N][GeCl_3]=PtCl_2[P(C_6H_5)_3]_2$ |
| 32 | $[(C_2H_5)_4N][SnCl_3]=PtCl_2[P(p-CH_3 . C_6H_4)_3]_2$ |
| 33 | $[(C_2H_5)_4N][SnCl_3]=PtCl_2[P(n-C_4H_9)_3]_2$ |
| 34 | $[(C_2H_5)_4N][SnCl_3]=PtCl_2[P(CH_3)_2C_6H_5]_2$ |

TABLE V

Analysis: Ni—54.7%, Al—11.4%, Cr—4.72%
Na—114 ppm

TABLE VI

|  |  |  |  |  | Mole % | | | | |
|---|---|---|---|---|---|---|---|---|---|
| Example | Olefin | Pressure psig | Rx. time (hrs) | Olefin conversion | Total yield aldehydes | Selectivity 1-aldehyde | Isomerization to 2,3-olefins | Reduction to alkane | Missing product |
| 35 | Propylene | 1260 | 6 | 95 | 90 | 87 | — | — | 5 |
| 36 | 1-Heptene | 1500 | 3 | 100 | 85 | 90 | 3.6 | 2.7 | 9 |
| 37 | 1-Undecene | 1260 | 5 | 100 | 86 | 96 | 10.8 | 3.2 | 0 |
| 38 | 1-Eicosene | 1500 | 3 | 100 | 57 | 89 | 12.3 | 6.5 | 25 |
| 39 | 2-Methyl-1-pentene | 1500 | 3 | 27 | 18 | 100 | 0 | 0 | 9 |
| 40 | 2-Heptene | 1500 | 3 | 6.5 | 6.5 | 3 | 0 | 0 | 0 |
| 41 | Cyclohexene | 1260[a] | 14 | 26 | 25 | — | — | 0 | 1 |

[a]Run at 108° C.

PROPYLENE HYDROFORMYLATION CATALYZED BY BIS(TRIPHENYLPHOSPHINE)PLATINUM(II) CHLORIDE DISPERSED TETRAETHYLAMMONIUM TRICHLOROSTANNATE(II)

| Cycle | n-Butyraldehyde selectivity (%) | Yield of isolated butyraldehydes (mol %) | Purity of isolated butyraldehydes (%) |
|---|---|---|---|
| I | 82 | 48 | 99 |
| II | 83 | 34 | 99 |
| III | 82 | 10 | 98 |

EXAMPLES 35-41

Hydroformylation of Olefins Catalyzed by PtCl$_2$(PPh$_3$)$_2$+SnCl$_2$—Effect of Olefin Structure Table VI which follows, shows the data obtained when the designated olefins are hydroformylated using the procedures of Example 1. All the examples shown in Table VI were carried out under the following conditions:

Solvent, methyl isobutyl ketone
Olefin, 0.88 moles per liter
Olefin/platinum molar ratio, 200/1
SnCl$_2$/PtCl$_2$(PPh$_3$)$_2$ molar ratio, 5/1
H$_2$/CO=1/1, 1500 psig or 1260 psig
Reaction temperature, 66° C.
Reaction time, 3-6 hours (exclusive of "cool down" periods)

The data in Table VI demonstrate that straight chain (linear) alpha-olefins are readily hydroformylated. Branched chain α-olefins are less easily hydroformylated, internal and cyclic olefins are the most difficult to hydroformylate using the catalysts of this invention under mild reaction conditions.

EXAMPLE 42

Preparation of Oxide-Supported Ni/Ar/Cr Catalyst

Sodium bicarbonate (320 gm) is dissolved in 3 liters of distilled water and the solution heated to 80° C. Hydrated nickel nitrate (291 gm), hydrated aluminum nitrate (187 gm) and chromium nitrate (40 gm) are also dissolved in 3 liters of distilled water, heated to 80° C., and the hot nitrate solution slowly added to the hot sodium bicarbonate solution. After stirring for 1 hour, the mixture is filtered and the solids washed eight times with 2 liters of hot distilled water. The filtrate of the last wash contained 2.0 ppm sodium. The solids are dried overnight at 110° C., calcined at 400° C. for 2 hours, and then prereduced under a nitrogen/hydrogen purge at 325° C.

Weight of catalyst prior to prereduction—110 gm

EXAMPLE 43

Preparation of Oxide-Supported Ni/Ba/Cr Catalyst

Sodium carbonate (255 gm) is dissolved in two liters of distilled water and the solution heated to 80° C. Hydrated nickel nitrate (436 gm), hydrated chromium nitrate (80 gm) and barium nitrate (157 gm) are also dissolved in 3 liters of distilled water, heated to 80° C., and the hot nitrate solution slowly added to the hot sodium carbonate solution. After stirring for 1 hour at 80° C., the mixture is filtered, and the solids washed eight times with 2 liters of hot water. The solids are dried overnight, calcined at 400° C. for 2 hours, and prereduced in a nitrogen/hydrogen stream at 325° C.

Weight of catalyst prior to prereduction—243 gm
Analysis: Ni—32.6%, Ba—32.2%, Cr—4.12%, Na—0.12%

EXAMPLE 44

Preparation of Oxide-Supported Ni/Mg/Cr Catalyst

Sodium carbonate (250 gm) is dissolved in three liters of distilled water and the solution heated to 80° C. Hydrated nickel nitrate (360 gm), hydrated magnesium carbonate (180 g) and hydrated chromium nitrate (24 gm) are dissolved in 1.5 liters of distilled water, heated to 80° C., and the hot nitrate solution slowly added to the hot sodium carbonate solution. After stirring at 80°-85° C. for 1 hour, the mixture is filtered, and the solids washed eight times with 2 liters of hot distilled water. The filtrate from the last washing contains 14 ppm Na. The solids are dried overnight, calcined at 400° C. for 2 hours, and prereduced in a stream of nitrogen/hydrogen at 325° C.

Weight of catalyst prior to prereduction—127 gm
Analysis: Ni—51.1%, Mg—11.9%, Cr—1.89%, Na—695 ppm

EXAMPLE 45

Reductive Amination of Octylaldehydes to Octylamines

An appropriately sized autoclave reactor equipped with heating, cooling, agitation, pressurizing means, a side ampoule system for introducing charges under operating conditions, and a sampling valve, is charged with deoxygenated methanol (100 ml). To the agitated solvent under a nitrogen surge is added 10 ml of octylaldehydes, prepared according to the procedure of Example 1 and containing 83 mole % n-octanol, plus 15 gm of oxide-supported nickel catalyst, prepared according to the procedure of Example 42. The reaction vessel is deoxygenated, 20 gm of ammonia injected in from the side ampoule, and the whole pressured to 1200 psig with hydrogen. The reaction mixture is then heated to 100° C., with agitation, and held at temperature for 4 hours.

On cooling and venting, the liquid product is separated from the solid catalyst by filtration and subjected to analysis by gas chromatography. Octylamines, 3.94 gm, 89% n-octylamine, are isolated by fractional distillation.

Gas chromatographic (gc) analysis revealed the following results:

| Conversion of octylaldehydes: | >98% |
|---|---|
| Yield of octylamines: | 48% |
| Selectivity to n-octylamine: | 89% |

EXAMPLES 46–53

Reductive Amination of Various Alkylaldehydes to Alkylamines Catalyzed by Nickel-Containing Catalysts Table VII which follows, shows the data obtained when the designated oxide-supported, nickel-containing catalysts of this invention, prepared according to the procedures of Examples 42–44, are screened for the reductive amination of $C_4$–$C_{14}$ l linear alkyl aldehydes to their corresponding linear $C_4$–$C_{14}$ alkyl primary amines by the procedure of Example 45. The paraffinic aldehyde substrates may be prepared by any of the procedures of Examples 1–41, but particularly those outlined in Example 1 using the homogeneous bis(triphenylphosphine)-platinum(II)-tin(II) chloride catalyst, and Example 26, using the dispersion of bis(triphenylphosphine)-platinum(II) chloride in tetraethylammonium trichlorostannate(II).

It may be noted from the data in Table VII that:

(a) $C_4$–$C_{14}$ Linear primary amines have been prepared by the procedure of Example 45 using all three oxide-supported nickel-containing catalysts described by Examples 42–44.

(b) Amination is achieved over a wide range of operating temperatures and pressures.

(c) The oxide-supported, nickel containing catalysts remain active following reductive amination, and may be recycled with additional linear paraffinic aldehyde feed to produce additional desired n-alkyl primary amine product in improved yields (eg. ≦80 mole %, Example 52).

EXAMPLE 54

Oxoamination of Propylene Catalyzed by a Combination of Bis(Triphenylphosphine) Platinum(II) Chloride-Stannous Chloride Plus Oxide-Supported Nickel Catalyst In this example the oxoamination of propylene to n-butylamine is carried out in accordance with the procedure of Example 1A except that the initial catalyst charge consists of a mixture of bis(triphenylphosphine)-platinum(II) chloride (1.0 mmole), tin(II) chloride (5.0 mmole),and oxide-supported nickel catalyst (5 g) prepared according to the procedure of Example 43. Said catalyst mixture is suspended in 60 ml of toluene, 8.4 g of propylene (200 mmole) injected from a side-ampoule, and the hydroformylation to n-butyraldehyde carried out in accordance with the conditions outlined in Examples 1 and 1A. Gas chromatographic analyses of the crude product liquid confirms the formation of n-butyraldehyde in 95% selectivity.

The crude product mixture is then treated with 30 ml of methanol, 10 g of ammonia is injected from the side ampoule, and the reductive amination carried out in accordance with the procedure of Examples 1A and 45. On cooling and venting, the liquid product is separated from the remaining solid catalyst by filtration and subjected to analysis by gas chromatography. n-Butylamine is obtained in 95% selectivity and >10 mole % yield basis $C_3H_6$ charged.

As the numerous examples of this invention indicate, the subject invention is advantageous in several respects compared to corresponding oxoamination of the prior art. For example, using various platinum(II) ligand stabilized-stannous chloride hydroformylation catalyst complexes, 1-alkenes can be hydroformylated to aldehydes at relatively mild reaction conditions of temperature and pressure. Furthermore, selectivities to the 1-aldehydes are generally excellent, and competing isomerization and reduction reactions are kept to a minimum. In addition, favorable (large) ratios of alkene to catalyst may be employed and generally most polar solvents are suitable as reaction media. Likewise the various oxide-supported nickel-containing amination catalysts, described herein, exhibit good specific activity and selectivity to linear alkyl primary amine during the reductive amination step, with improved performances upon recycle.

Finally, the invention is quite advantageous in that numerous substitutions, modifications and changes can be made without departing from the inventive concept. However, the scope of the subject invention can best be understood by examining the claims which follow, in conjunction with the preceding specification.

TABLE VII

| | Nickel-containing catalyst, prepared by method of: | Aldehyde charge | Amination | | | Alkyl amine product | |
|---|---|---|---|---|---|---|---|
| Example | | | Temp (°C.) | Pressure (psig) | Aldehyde conv (%) | Composition | Yield (mol %) |
| 46 | 43 | n-Valeraldehyde | 120 | 1500 | >98 | n-Amylamine | 77 |
| 47 | 43 | n-Butyraldehyde | " | " | >98 | n-Butylamine | 64 |
| 48 | 42 | n-Octylaldehyde | " | " | >98 | n-Octylamine | 52 |
| 49 | 44 | " | 100 | 500 | >98 | " | 48 |
| 50 | 42 | " | " | 100 | >98 | " | 28 |
| 51 | 42 | " | 50 | 3000 | 80 | " | <10 |
| 52 | 42 - recycled after use in Example 50 | " | 120 | 1200 | >98 | " | 87 |
| 53 | 44 | n-Tetradecyl-aldehyde | 120 | 1500 | >98 | n-Tetradecylamine | >10 |

We claim:
1. A process for preparing linear alkyl primary amines by the catalytic oxoamination of linear alpha olefin substrates containing 2 to 30 carbon atoms, by the steps of first producing primarily linear aldehydes then preparing primarily the corresponding amines, by the steps of:
  (a) forming a hydroformylation reaction mixture of olefin substrate, carbon monoxide, hydrogen and from about 0.001 to 0.1 moles of a three-component, ligand-stabilized, platinum (II) halide catalyst per mole of olefin substrate, said catalyst being selected from the group consisting of:
  $PtCl_2[P(C_6H_5)_3]_2 + SnCl_2$
  $PtCl_2[P(p-CH_3.C_6H_4)_3]_2 + SnCl_2$
  $PtCl_2[P(n-C_4H_9)_3]_2 + SnCl_2$
  $PtCl_2[P(C_6H_5)_3]_2 + SnCl_4$
  $PtCl_2[P(C_6H_5)_3]_2 + GeCl_2$
  $PtCl_2[P(CH_3)_2C_6H_5]_2 + SnCl_2$
  $PtCl_2[Ph_2AsCH_2CH_2AsPH_2] + SnCl_2$
  $PtCl_2[P(OC_6H_5)_3]_2 + SnCl_2$
  $PtCl_2[As(C_6H_5)_3]_2 + SnCl_2$
  $PtCl_2[S(C_6H_5)_2]_2 + SnCl_2$
  $PtBr_2[P(C_6H_5)_3]_2 + SnBr_2$
  $PtCl_2[PH_2PCH_2CH_2PPh_2] + SnCl_2$
  $PtCl_2[Sb(C_6H_5)_3]_2 + SnCl_2$
  $PtCl_2(o\text{-Phenanthroline}) + SnCl_2$
  $PtCl_2[P(C_6H_5)_3]_2 + [Cl_3Sn][N(C_2H_5)_4]$
  $PtCl_2[P(C_6H_5)_3]_2 + [Cl_3Sn][P(C_6H_5)CH_2Cl]$
  $PtCl_2[P(C_6H_5)_3]_2 + [Cl_3Sn][N(n-C_4H_9)_4]$
  $PtCl_2[P(C_6H_5)_3]_2 + [Cl_3Sn][As(C_6H_5)_4]$
  $PtCl_2[P(C_6H_5)_3]_2 + [Cl_3Sn][N(C_7H_{15})_4]$
  $PtCl_2[P(C_6H_5)_3]_2 + [Cl_3Ge][N(C_2H_5)_4]$
  $PtCl_2[P(p-CH_3.CH_3.C_6H_4)_3]_2 + [Cl_3Sn][N(C_2H_5)_4]$
  $PtCl_2[P(n-C_4H_9)_3]_2 + [Cl_3Sn][N(C_2H_5)_4]$
  the carbon monoxide and hydrogen being present in quantities sufficient to satisfy the stoichiometry of the hydroformylation reaction,
  (b) pressurizing the hydroformylation reaction mixture between about 100 psig to about 3000 psig and heating the pressurized reaction mixture at about 25° C. to about 125° C. until a major amount of linear alkyl primary aldehyde products and a minor amount of non-linear alkyl aldehyde products are formed, and
  (c) contacting said linear alkyl aldehyde products with at least sufficient hydrogen and ammonia to satisfy the stoichiometry of reducing the linear alkyl aldehyde to linear alkyl primary amine product, pressurizing between about 100 psig to about 3000 psig and heating said linear alkyl aldehyde from about 25° to about 200° C. in the presence of oxide-supported nickel catalysts containing from 5% up to 75 weight % nickel in addition to oxides of two or more other metals selected from the group consisting of magnesium, barium, aluminum and chromium, until a major quantity of linear alkyl primary amine product is formed, and
  (d) isolating the linear alkyl primary amine product contained therein,
wherein the three-component, ligand-stabilized, platinum (II) halide catalyst and the oxide-supported nickel catalyst are added to the reaction mixture prior to the aldehyde forming reaction and are present during both the conversion of olefin substrates to alkyl aldehyde products and during the amination of said aldehydes to linear alkyl primary amines.

2. A selective process for preparing linear alkyl amines from linear alkyl alpha-olefins containing 2–30 carbon atoms by reaction in the presence of a two-member catalyst system, said selective process being conducted in the presence of both members of the two-member catalyst system without removing either of the catalysts of the two-member catalyst system or without isolating any intermediate from the reaction mixture by the steps of:
  (a) forming a hydroformylation reaction mixture of alkyl alpha olefin substrate, carbon monoxide, hydrogen, inert solvent, and both of the two different members of the two-member catalyst comprising (i) from about 0.001 to 0.1 moles of a three-component ligand stabilized platinum (II) halide catalyst per mole of the linear alpha olefin, and (ii) at least a stoichiometric amount of an oxide-supported, nickel-containing catalyst;
  said three-component, ligand stabilized platinum (II) halide catalyst being selected from the group consisting of:
  $PtCl_2[P(C_6H_5)_3]_2 + SnCl_2$
  $PtCl_2[P(p-CH_3.C_6H_4)_3]_2 + SnCl_2$
  $PtCl_2[P(n-C_4H_9)_3]_2 + SnCl_2$
  $PtCl_2[P(C_6H_5)_3]_2 + SnCl_4$
  $PtCl_2[P(C_6H_5)_3]_2 + GeCl_2$
  $PtCl_2[P(CH_3)_2C_6H_5]_2 + SnCl_2$
  $PtCl_2[Ph_2AsCH_2CH_2AsPH_2] + SnCl_2$
  $PtCl_2[P(OC_6H_5)_3]_2 + SnCl_2$
  $PtCl_2[As(C_6H_5)_3]_2 + SnCl_2$
  $PtCl_2[S(C_6H_5)_2]_2 + SnCl_2$
  $PtBr_2[P(C_6H_5)_3]_2 + SnBr_2$
  $PtCl_2[PH_2PCH_2CH_2PPh_2] + SnCl_2$
  $PtCl_2[Sb(C_6H_5)_3]_2 + SnCl_2$
  $PtCl_2(o\text{-Phenanthroline}) + SnCl_2$
  $PtCl_2[P(C_6H_5)_3]_2 + [Cl_3Sn][N(C_2H_5)_4]$
  $PtCl_2[P(C_6H_5)_3]_2 + [Cl_3Sn][P(C_6H_5)CH_2Cl]$
  $PtCl_2[P(C_6H_5)_3]_2 + [Cl_3Sn][N(n-C_4H_9)_4]$
  $PtCl_2[P(C_6H_5)_3]_2 + [Cl_3Sn][As(C_6H_5)_4]$
  $PtCl_2[P(C_6H_5)_3]_2 + [Cl_3Sn][N(C_7H_{15})_4]$
  $PtCl_2[P(C_6H_5)_3]_2 + [Cl_3Ge][N(C_2H_5)_4]$
  $PtCl_2[P(p-CH_3.CH_3.C_6H_4)_3]_2 + [Cl_3Sn][N(C_2H_5)_4]$
  $PtCl_2[P(n-C_4H_9)_3]_2 + [Cl_3Sn][N(C_2H_5)_4]$
  the carbon monoxide and hydrocarbon being present in quantities sufficient to satisfy the stoichiometry of the hydroformylation reaction,
  (b) pressurizing the hydroformylation reaction mixture between about 100 psig to about 3000 psig and heating the pressurized reaction mixture at about 25° C. to about 125° C. until a major amount of linear alkyl primary aldehyde products and a monor amount of non-linear alkyl aldehyde products are formed, and
  (c) contacting said linear alkyl aldehyde products with at least sufficient hydrogen and ammonia to satisfy the stoichiometry of reducing the linear alkyl aldehyde to linear alkyl primary amine product, pressurizing between about 100 psig to about 3000 psig and heating said linear alkyl aldehyde from about 25° to about 200° C. in the presence of said oxide-supported nickel catalyst containing from 5% up to 75 weight % nickel in addition to oxides of two or more other metals selected from the group consisting of magnesium, barium, aluminum and chromium, until a major quantity of linear alkyl primary amine product is formed, and (d) isolating the linear alkyl primary amine product contained therein.

3. The process of claim 1 wherein the platinum hydroformylation catalyst consists of a dispersion of ligand-stabilized platinum(II) halide complex in a low-melting quaternary alkyl ammonium salt of trichlorostannate(II).

4. The process of claim 1 wherein the platinum hydroformylation catalyst consists of a dispersion of bis(triphenylphosphine)platinum(II) chloride in tetraethylammonium trichlorostannate(II).

5. The process of claim 1 wherein the reaction is carried out in the presence of an inert solvent.

6. The process of claim 1 wherein the contacting step to produce linear alkyl primary amines is carried out in the presence of an inert solvent.

7. The process of claim 5 wherein the inert solvent is selected from the group of solvents consisting of acetone, methyl ether ketone, methyl isopropyl ketone, acetophenone, benzene and toluene.

8. The process of claim 6 wherein the inert solvent is selected from the group of solvents consisting of methanol, ethanol, isopropanol and tert. butanol.

* * * * *

UNITED STATES PATENT AND TRADEMARK OFFICE
CERTIFICATE OF CORRECTION

PATENT NO. : 4,299,985
DATED : November 10, 1981
INVENTOR(S) : J. Knifton and P. Moss It is certified that error appears in the above—identified patent and that said Letters Patent is hereby corrected as shown below:

Col. 5, line 6, the formula should read $$[(C_2H_5)_4N][SnCl_3] - PtCl_2[P(CH_3)_2C_6H_5]_2$$

Col. 7, line 15, cancel "$\frac{1}{2}$", insert -- 1/2 --;

Col. 15, line 47, " $\leqq$ ", insert -- > --.

Signed and Sealed this

Twentieth Day of April 1982

[SEAL]

Attest:

GERALD J. MOSSINGHOFF

*Attesting Officer*     *Commissioner of Patents and Trademarks*